(12) United States Patent
Jabbari (10) Patent No.: US 10,894,019 B2
(45) Date of Patent: Jan. 19, 2021

(54) DRUG DELIVERY SYSTEM AND METHOD FOR TARGETING CANCER STEM CELLS

(71) Applicant: UNIVERSITY OF SOUTH CAROLINA, Columbia, SC (US)

(72) Inventor: Esmaiel Jabbari, Rockville, MD (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 16/057,954

(22) Filed: Aug. 8, 2018

(65) Prior Publication Data

US 2019/0054034 A1 Feb. 21, 2019

Related U.S. Application Data

(60) Provisional application No. 62/545,514, filed on Aug. 15, 2017.

(51) Int. Cl.
| | |
|---|---|
| *A61K 9/51* | (2006.01) |
| *A61K 31/337* | (2006.01) |
| *A61P 35/00* | (2006.01) |
| *A61K 47/69* | (2017.01) |
| *A61K 31/704* | (2006.01) |
| *A61K 45/06* | (2006.01) |

(52) U.S. Cl.
CPC .......... *A61K 9/5146* (2013.01); *A61K 31/337* (2013.01); *A61K 31/704* (2013.01); *A61K 45/06* (2013.01); *A61K 47/6923* (2017.08); *A61K 47/6929* (2017.08); *A61P 35/00* (2018.01)

(58) Field of Classification Search
CPC .............. A61K 31/337; A61K 2300/00; A61K 31/704; A61K 45/06; A61K 47/6923; A61P 35/00
See application file for complete search history.

(56) References Cited

U.S. PATENT DOCUMENTS

| | | | |
|---|---|---|---|
| 5,037,883 A | 8/1991 | Kopecek et al. |
| 6,342,221 B1 | 1/2002 | Thorpe et al. |
| 6,346,349 B1 | 2/2002 | Briscoe et al. |
| 6,348,209 B2 | 2/2002 | Placke et al. |
| 7,374,774 B2 | 5/2008 | Bowlin et al. |
| 7,531,503 B2 | 5/2009 | Atala et al. |
| 7,737,131 B2 | 6/2010 | Kiick et al. |
| 7,759,082 B2 | 7/2010 | Bowlin et al. |
| 7,767,221 B2 | 8/2010 | Lu et al. |
| 8,066,932 B2 | 11/2011 | Xu |
| 8,071,722 B2 | 12/2011 | Kaplan et al. |
| 8,202,551 B2 | 6/2012 | Li et al. |
| 8,267,992 B2 | 9/2012 | Atanasoska et al. |
| 8,449,622 B2 | 5/2013 | McKay |
| 8,551,390 B2 | 10/2013 | Jun et al. |
| 8,586,345 B2 | 11/2013 | Simpson et al. |
| 8,691,543 B2 | 4/2014 | Gaudette et al. |
| 2003/0215624 A1 | 11/2003 | Layman et al. |
| 2004/0229333 A1 | 11/2004 | Bowlin et al. |
| 2006/0067969 A1 | 3/2006 | Lu et al. |
| 2006/0204441 A1 | 9/2006 | Atala et al. |
| 2006/0204445 A1 | 9/2006 | Atala et al. |
| 2006/0204539 A1 | 9/2006 | Atala et al. |
| 2007/0018361 A1 | 1/2007 | Xu et al. |
| 2007/0269481 A1 | 11/2007 | Li et al. |
| 2008/0038352 A1 | 2/2008 | Simpson et al. |
| 2008/0065210 A1 | 3/2008 | McKay et al. |
| 2008/0102145 A1 | 5/2008 | Kim et al. |
| 2008/0109070 A1 | 5/2008 | Wagner et al. |
| 2008/0159985 A1 | 7/2008 | Bowlin et al. |
| 2008/0213389 A1 | 9/2008 | Lelkes et al. |
| 2008/0220042 A1 | 9/2008 | Hashi et al. |
| 2008/0220054 A1 | 9/2008 | Shastri et al. |
| 2010/0047309 A1 | 2/2010 | Lu et al. |
| 2013/0338791 A1 | 12/2013 | McCullen et al. |

OTHER PUBLICATIONS

Qin et al. Frontiers in Pharmacology 2017; 8(1) 1-15.*
Ghanbari et al. (Macromol. Rapid Commun. (2011), 32, 1032-1046).*
Kickelbick (Struct Bond 2013).*
*Li et al (Frontiers in Pharmacology, 1-12).*
Li et al. Adv. Funct. Mater. 2011, 21, 287-294).*
Burke et al (J Mol Biomarkers Diagn 2012, S:8, 1-8).*
Ayandele et al. (Nanomaterials 2012, 2,445-475).*
Lee et al Am J Cancer Res 2016;6(5):1118-1134.*
Singh et al. (Exp. Mol Pathl. 2009; 86(3): 215-233).*
Krishnamurthy et al (Nanomedicine, 2015); 10(1):143-160.*
Adam, et al., "Signaling through PI3K/AKT mediates stretch and PDGF-BB-dependent DNA synthesis in bladder smooth muscle cells," *J Urol* 169, (2003), p. 2388.
Aklonis, et al., "Introduction to polymer viscoelasticity." New York: Wiley-Interscience, (1972).
Arai, et al., "Tie2/Angiopoietin-1 Signaling Regulates Hematopoietic Stem Cell Quiescencein the Bone Marrow Niche," *Cell*, 118, (2004), pp. 149-161.
Badve, et al., "Breast-cancer stem cells-beyond semantics," *Lancet Oncol* 13, (2012), p. e43.
Bhat-Nakshatri, et al., "SLUG/SNAI2 and tumor necrosis factor generate breast cells with CD44+/CD24-phenotype," *BMC Cancer* 10 (2010), p. 411.
Biddle, et al., "Cancer stem cells and EMT in carcinoma," *Cancer Metastasis Rev*, PMID: 22302111, (2012).

(Continued)

*Primary Examiner* — Shirley V Gembeh
(74) *Attorney, Agent, or Firm* — Dority & Manning, P.A.

(57) ABSTRACT

Systems and methods for targeting specific cancer cell subpopulations present in tumor tissue are described. A system can include a first component for specifically targeting cancer stem cells and a second component for specifically targeting differentiated cancer cells. A system can include a drug conjugated to small (e.g., 5-20 nm) nanoparticles, e.g., polyhedral oligomeric silsequioxane nanoparticles. The small nanoparticles can be preferentially taken up by cancer stem cells via macropinocytosis and can release a toxic payload within the cancer stem cells without triggering the efflux pump. A system can include a second component that targets differentiated cancer cells, e.g., a free drug or a drug encapsulated in nanoparticles.

6 Claims, 5 Drawing Sheets

(56) References Cited

OTHER PUBLICATIONS

Britton, et al., "Breast cancer, side population cells and ABCG2 expression," *Cancer Lett* 323, (2012), p. 97.

Bryant, et al., "Hydrogel properties influence ECM production by chondrocytes photoencapsulated in poly(ethylene glycol) hydrogels "*Jnl. Biomed Mater Res.*, (2002) 59, pp. 63-72.

Buxton, et al., "Design and Characterization of Poly(Ethylene Glycol) Photopolymerizable Semi-Interpenetrating Networks for Chondrogenesis of Human Mesenchymal Stem Cells," *Tissue Engineering*, (2007) 13, pp. 2549-2560.

Castano, et al., "The tumor macroenvironment and systemic regulation of breast cancer progression," *Int J Dev Biol* (2011) 55, p. 889.

Chen, et al., "Geometric Control of Cell Life and Death,"*Science*, (1997) 276, pp. 1425-1428.

Chirila, et al., "Poly(2-hydroxyethyl methacrylate) sponges as implant materials: in vivo and in vitro evaluation of cellular invasion," *Biomaterials.*, (1993) 14, (1) pp. 26-38.

Cushing, et al.; "Materials science: hydrogel cell cultures," *Science*, 316, 1133, 2007.

Dawson, et al., "Biomaterials for stem cell differentiation," *Adv. Drug Deliv.Reviews*, (2008) 60, pp. 215-228.

Debnath, et al., "Modelling Glandular Epithelial Cancers in Three-Dimensional Cultures,"*Nature Reviews—Cancer*, (2005) 5, pp. 675-688.

Del Vecchio, et al., "Epidermal growth factor receptor variant III contributes to cancer stem cell phenotypes in invasive breast carcinoma," *Cancer Res*, 72, (2012), p. 2657.

Discher, et al., "Tissue Cells Feel and Respond to the Stiffness of Their Substrate," *Science*, (2005) 310, pp. 1139 (6 pages).

Doroski, et al., "Cyclic Tensile Culture Promotes Fibroblastic Differentiation of Marrow Stromal Cells Encapsulated in Poly(Ethylene Glycol)-Based Hydrogels," *Tissue Engineering: Part A*, (2010) 16, pp. 3457-3466.

Elisseeff, et al., "Photoencapsulation of chondrocytes in poly(ethylene oxide)-based semi-interpenetrating networks," *J. Biomed Mater Res.*, (2000) 51, pp. 164-171.

Engler, et al., "Embryonic cardiomyocytes beat best on a matrix with heart-like elasticity: scar-like rigidity inhibits beating," *Jnl. of Cell Sci.*, (2008) 121, pp. 3794-3802.

Engler, et al., "Extracellular matrix elasticity directs stem cell differentiation,"*j. Musculoskelet Neuronal Interact*, (2007) 7 (4), p. 335.

Engler, et al., "Matrix Elasticity Directs Stem Cell Lineage Specification," *Cell*, (2006) 126, pp. 677-689.

Fernandez-Gonzalez, et al., "In situ analysis of cell populations: long-term label-retaining cells," *Methods Mol Biol* 621, (2010), p. 1.

Fillmore, et al., "Human breast cancer cell lines contain stem-like cells that self-renew, give rise to phenotypically diverse progeny and survive chemotherapy," *Breast Cancer Res* 10, (2008), p. R25.

Flanagan, et al., "Neurite branching on deformable substrates," *Neuroreport* 13, (2002), p. 2411.

Floor, et al., "Cancer cells in epithelial-to-mesenchymal transition and tumor-propagating-cancer stem cells: distinct, overlapping or same populations," *Oncogene* 30, (2011), p. 4609.

Gill, et al., "The association of mammographic density with ductal carcinoma in situ of the breast: The Multiethnic Cohort," *Breast Cancer Res* 8, (2006), p. R30.

Grange, et al., "Sca-1 identifies the tumor-initiating cells in mammary tumors of BALB-neuT transgenic, mice," *Neoplasia* 10, (2008), p. 1433.

Gupta, et al., "Identification of selective inhibitors of cancer stem cells by high-throughput screening," *Cell* 138, (2009), p. 645.

Habel, et al., "Mammographic density and breast cancer after ductal carcinoma in situ," *J Natl Cancer Inst* 96, (2004), p. 1467.

Haycock, J.W., "3D cell-culture: A review of current approaches and techniques," *Methods Mol Biol*, 695, 1, (2011).

He, et al., "Cellular and Molecular Regulation of hematopoietic and Intestinal Stem Cell Behavior," *Ann. N.Y. Acad. Sci.*, (2005) 1049, pp. 28-38.

He, et al., "Material properties and cytocompatibility of injectable MMP degradable poly(lactide ethylene oxide fumarate) hydro gel as a carrier for marrow stromal cells," *Biomacromolecules* 8, (2007), p. 780.

He, et al., "Combined effect of osteopontin and BMP-2 derived peptides grafted to an adhesive hydrogel on osteogenic and vasculogenic differentiation of marrow stromal cells," *Langmuir* 28, (2012), p. 5387.

Heddleston, et al., "Hypoxia inducible factors in cancer stem cells," *Br J Cancer* 102, (2010), p. 789.

Hsu, et al., "A family business: Stem cell progeny join the niche to regulate homeostasis," *Nat Rev Mol Cell Biol* 13, (2012), p. 103.

Huebsch, et al., "Harnessing traction-mediated manipulation of the cell/matrix interface to control stem-cell fate,"*Nature Materials*, (2010) 9, pp. 518-526.

Kai, et al., "Breast cancer stem cells," *Breast Cancer* 17, (2010), p. 80.

Katoh, M. "Networking of WNT, FGF, Notch, BMP, and Hedgehog signaling pathways during carcinogenesis," *Stem Cell Rev* 3, (2007), p. 30.

Keung, et al., "Presentation Counts: Microenvironmental Regulation of Stem Cells by Biophysical and Material Cues," *Annu. Rev. cell Dev. Biol.* (2010) 26, pp. 533-556.

Kim, et al., "OCT4 Expression Enhances Features of Cancer Stem Cells in a Mouse Model of Breast Cancer," *Lab Anim Res*, 27(2), (2011), pp. 147-152.

Korkaya, et al., "Breast cancer stem cells, cytokine networks, and the tumor microenvironment," *Journal Clin Invest* 121, (2011), p. 3804.

Krohn, et al., "CXCR4 receptor positive spheroid forming cells are responsible for tumor invasion in vitro," *Cancer Lett* 280 (2009), p. 65.

Leal-Egana, et al., "Determination of pore size distribution at the cell-hydrogel interface," *Journal Nanobiotechnol* 9, (2011), p. 24.

Lee, et, al., "Gel microstructure regulates proliferation and differentiation of MC3T3-E1 cells encapsulated in alginate beads."*Acta Biomaterialia*, (2012) 8, pp. 1693-1702.

Levental, et al., "Matrix crosslinking forces tumor progressions by enhancing integrity signaling," *Cell* 139, (2009), p. 891.

Li, et al., "Normal Stem cells and cancer stem cells." *Cancer Res* 66, (2006), pp. 4553-4557, 6458.

Liang, et al., "A cell-instructive hydrogel to regulate malignancy of 3D tumor spheroids with matrix rigidity," *Biomaterials* 32, (2011), p. 9308.

Liu, et al., "Identification of tumorsphere- and tumor-initiating cells in HER2/Neu-induced mammary tumors," *Cancer Res* 67, (2007), p. 8671.

Liu, et al., "Biomimetic hydrogels for chondrogenic differentiation of human mesenchymal stem cells to neocartilage," *Biomaterials*, (2010) 31, pp. 7298-7307.

Livak, et al., "Analysis of relative gene expression data using real-time quantitative PCR and the 2(-Delta Delta C(T)) Method," *Methods* 25,(2001), p. 402.

Masters, et al., "Designing scaffolds for valvular interstitial cells: Cell adhesion and function on naturally derived materials," *Wiley Periodicals, Inc.*, (2004) [Published online Aug. 18, 2004 in Wiley InterScience (www.interscience.wiley.com). DOI: 10.1002/jbm.a. 30149] (9 pages).

Mironi-Harpaz, et al., "Photopolymerization of cell-encapsulating hydrogels: Crosslinking efficiency versus cytotoxicity," *Acta Biomaterialia* (2012) 8, pp. 1838-1848.

Moeinzadeh, et al., "Synthesis and gelation characteristics of photo-crosslinkable star poly(ethylene oxide-co-lactide-glycolide acrylate) macromonomers." *Polymer*, 52, 3887, 2011.

Nemir, et al., "Synthetic Materials in the Study of Cell Response to Substrate Rigidity," *Annals of Biomedical Engineering Society* (2009) 38, (1), pp. 2-20.

Pampaloni, et al., "The third dimension bridges the gap between cell culture and live tissue," *Nature Reviews | Molecular Cell Biology*, (2007) 8, pp. 839-845.

(56) References Cited

OTHER PUBLICATIONS

Papadopoulos, et al., "Injectable and photopolymerizable Tissue-Engineered Auricular Cartilage Using Poly(Ethylene Glycol) Dimethacrylate Copolymer Hydrogels,"*Tissue Engineering: Part A*, (2011) 17 (1,2), pp. 161-169.
Parekh, et al., "Modulus-driven differentiation of marrow stromal cells in 3D scaffolds that is independent of myosin-based cytoskeletal tension." *Biomaterials*, (2011) 32, pp. 2256-2264.
Paszek, et al., "Tensional homeostasis and the malignant phenotype," *Cancer Cell* 8, (2005), p. 241.
Pek, et al., "The effect of matrix stiffness on mesenchymal stem cell differentiation n a 3D thixotropic gel," *Biomaterials* (2010) 31, pp. 385-391.
Peng, et al., "Long-term sphere culture cannot maintain a high ratio of cancer stem cells: A mathematical model and experiment," *PLoS One* 6, (2011), p. e25518.
Peppas, et al., "Characterization of the crosslinked structure of hydrogels," In: Peppas, N.A., ed. Hydrogel in medicine and pharmacy. Boca Raton: CRC Press, 1986, pp. 27-56.
Petersen, et al., "Interaction with basement membrane serves to rapidly distincuish growth and differentiation pattern of normal and malignant human breast epithelial cells," *Proc Natl Acad Sci USA* 89 (1992), p. 9064.
Provenzano, et al., "Matrix density-induced mechanoregulation of breast cell phenotype, signaling and gene expression through a FAK-ERK linkage,"*Oncogene*, (2009) 23, pp. 4326-4343.
Raof, et al., "Bioengineering embryonic stem cell microenvironments for exploring inhibitory effects on metastatic breast cancer cells," *Biomaterials*, (2011) 32, pp. 4130-4139.
Rehfeldt, et al., "Cell responses to the mechanochemical microenvironment—Implications for regenerative medicine and drug delivery," *Adv. Drug Deliv. Reviews*, (2007) 59, pp. 1329-1339.
Rhim, et al., "EMT and dissemination precede pancreatic tumor formation," *Cell* 148, (2012), p. 349.
Samani, et al., "Elastic moduli of normal and pathological human breast tissues: An inversion-technique-based investigation of 169 samples," *Phys Med Biol* 52, (2007), p. 1565.
Sawhney, et al., "Interfacial photopolymerization of poly(ethylene glycol)-based hydrogels upon alginate-poly (l-lysine) microcapsules for enhanced biocompatibility," *Biomaterials*, (1993) 14, (13) pp. 1008-1016.
Schefe, et al., "Quantitative real-time RT-PCR data analysis: current concepts and the novel "gene expression's CT difference" formula," *Journal Mol Med* (Berl) 84, (2006), p. 901.
Schrader, et al., "Matrix Stiffness Modulates Proliferation, Chemotherapeutic Response, and Dormancy in Hepatocellular Carcinoma Cells," *Hepatology*, (2011) 53 (4), pp. 1192-1205.
Silverstein, et al., "Spectrometric identification of organic compounds." New York: John Wiley, (1991).
Singhvi, et al., "Engineering cell shape and function," *Science*, 264, (1994), p. 696.
Smith, et al., "Three-Dimensional Culture of Mouse Renal Carcinoma Cells in Agarose Macrobeads Selects for a Subpopulation of Cells with Cancer Stem Cell or Cancer Progenitor Properties," *Cancer Res*; (2011) 71, (3) pp. 716-724.
Soeda, et al., "Hypoxia promotes expansion of CD133-positive glioma stem cells through activation of HIF-1 alpha," *Oncogene* 28, (2009), p. 3949.
Sun, et al., "Forcing Stem Cells to Bheave: A Biophysical Perspective of the Cellular Microenvironment,"*Annu. Rev. Biophys.*, (2012) 41, pp. 519-542.
Tao, et al., "Imagable 4TI model for the study of late stage breast cancer," *BMC Cancer*, 8,228, 2008.
Tilghman, et al., "Matrix Rigidity Regulates Cancer Cell Growth and Cellular Phenotype," *PLoS ONE*, (2010) 5, (9), e12905. doi: 10.1371/journal.pone.0012905 (13 pages).
Tschumperlin, et al., "Mechanotransduction through growth-factor shedding into the extracellular space," *Nature* 429, (2004), p. 83.
Vargo-Gogola, et al., "Modelling breast cancer: one size does not fit all," *Nat Rev Cancer* 7, (2007), p. 659.
Verbridge, at al.; "Tissue-engineered three-dimensional tumor models to study tumor angiogenesis," *Tissue Eng.*, A 16, 2147, 2010.
Vincent, et al., "Basic fibroblast growth factor mediates transduction of mechanical signals when articular cartilage is loaded," *Arthritis Rheum* 50, (2004), p. 526.
Weiswald, et al., "In situ protein expression in tumour spheres: development of an immunostaining protocol for confocal microscopy," *BMC Cancer* 10, (2010), p. 106.
Welm, et al., "Isolation and characterization of functional mammary gland stem cells," *Cell Prolif Suppl* 1, (2003), p. 17.
Woodward, et. al., "On mammary stem cells," *Journal Cell Sci* 118, (2005), p. 3585.
Yang, et al., "Effect of CD44 Binding Peptide Conjugated to an Engineered Inert Matrix on Maintenance of Breast Cancer Stem Cells and Tumorsphere Formation", *PLoS ONE*, Mar. 2013, vol. 8, Issue 3, e59147 (15 pages). (Abstract Only).
Yang, et al., "Three-Dimensional-Engineered Matrix to Study Cancer Stem Cells and Tumorsphere Formation: Effect of Matrix Modulus," *Tissue Engineering Part A*, vol. 19, No. 5-6, 2013, pp. 669-685.
Yip, et al., "A multicellular 3D heterospheroid model of liver tumor and stromal cells in collagen gel for anti-cancer drug testing," *Biochemical and Biophysical Research Communications* 433 (2013), pp. 327-332.
Yu, et al., "Kruppel-like factor 4 (KLF4) is required for maintenance of breast cancer stem cells and for cell migration and invasion," *Oncogene* 30 (2011), p. 2161.
Zaman, et al., "Migration of tumor cells in 3D matrices is governed by matrix stiffness along with cell-matrix adhesion and proteolysis," *PNAS*, (2006) 103 (29), pp. 10889-10894.
Zeisberg, et al., "Biomarkers for epithelial-mesenchymal transitions," *Journal Clin Invest* 119, (2009), p. 1429.

\* cited by examiner

DRUG DELIVERY SYSTEM AND METHOD FOR TARGETING CANCER STEM CELLS

CROSS REFERENCE TO RELATED APPLICATION

This application claims filing benefit of U.S. Provisional Patent Application Ser. No. 62/545,514 having a filing date of Aug. 15, 2017, which is incorporated herein by reference for all purposes.

STATEMENT REGARDING FEDERALLY SPONSORED RESEARCH OR DEVELOPMENT

This invention was made with government support under grant no. 1403545 awarded by the National Science Foundation. The government has certain rights in the invention.

BACKGROUND

An estimated 12 million new cancer cases are diagnosed worldwide every year with 1.5 million of those new cases in the US alone. Moreover, cancer is estimated to cause 8 million deaths every year worldwide with approximately 500,000 of those occurring in the US. The overall costs of cancer are estimated at $125 billion/year and this could increase to $200 billion by the year 2020. A major contributing factor to mortality in cancer patients as well as treatment costs is recurrence in the form of relapse (after surgery or therapy) and development of resistance to therapy.

Cancer recurrence is related to the existence of cancer stem cells (CSCs) in the tumor tissue. Normal stem cells and CSCs use similar signaling pathways to maintain their 'stemness.' However, they are believed to respond to environmental cues differently. Under normal conditions, stem cells are dormant and their proliferation and differentiation is inhibited unless they are activated by injury to the tissue, but CSCs, due to cell mutations, are self-sufficient with respect to proliferation. It has been proposed that in the case of CSCs the stem cell niche supports cell proliferation, as opposed to inhibition of proliferation in normal stem cells. In addition, CSCs exhibit high expression of ATP-binding cassette (ABC) transporter proteins associated with drug resistance and as such show resistance to many therapies that are effective against other cells in the tumor cell population. Accordingly, although CSCs are present in a very small population in tumor tissue, generally less than 1% of the total tumor cell population, the CSCs that survive after therapy can grow into a heterogeneous population of colonies with a range of invasiveness with high resistance to therapy.

Typically, after cancer therapy the bulk of a tumor will shrink to less than 1% of its initial volume, but the remaining tumor tissue becomes enriched with CSCs that are highly resistant to future therapies. Consistent with this model, 15% of breast cancer patients are diagnosed with the most aggressive triple negative breast cancer (TNBC) having the highest sub-population of CSCs. These patients show a survival rate of 77% after 5 years, compared to 93% for other breast cancer subtypes.

The differentiated sub-population of cancer cells tend to adhere to the extracellular matrix (ECM) and they generally take up and respond well to cancer drugs like Doxorubicin or Paclitaxel. Unfortunately, many such cancer drugs have been shown to be ineffective against the most aggressive CSC sub-population of cancer cells. The sub-population of CSCs can form a colony starting from a single self-renewing cell and adhere to other cells in the colony as the colony grows, rather than adhering to the ECM as do differentiated cancer cells. This combined with the fact that CSCs are often either resistant or do not respond at all to certain cancer drugs is believed to lead to the survival of CSCs during typical cancer therapy. As a result, tumors relapse after therapy with much higher aggressiveness, often leading to patient death.

What are needed in the art are methods and systems that can be utilized for delivery of effective agents to both the differentiated cancer cells and the CSC subpopulation of tumor tissue to improve elimination of malignant/mutated cells in the tumor tissue.

SUMMARY

According to one embodiment, disclosed is a drug delivery system that specifically targets CSCs. The system includes a biologically active agent that directly or indirectly targets CSCs. In addition, the agent is conjugated to a nanoparticle that is within a narrow size range so as to be taken up by the CSCs in a tumor tissue. In particular, the nanoparticle can have a size in a range of from about 5 nm to about 20 nm. The nanoparticle can be, for example, a silica-based nanoparticle such as a polyhedral oligomeric silsequioxane (POSS)-based nanoparticle.

In one embodiment, the system can target both differentiated cancer cells and the CSC subpopulation in the tumor tissue. In this embodiment, the system can include a first agent conjugated to a nanoparticle of a size that targets the CSCs in combination with a second agent that can be the same or different from the first agent. The second agent can be in a form that targets differentiated cancer cells, for instance in free form, as a conjugate with an antibody for targeting differentiated cancer cells, or encapsulated in a degradable nanoparticle that differs from the CSC-targeted nanoparticle.

Also disclosed is a method for targeting both CSCs and differentiated cancer cells that are present in an area, e.g., a tumor tissue. The method can include targeting the area with the drug delivery system, upon which the first agent carried by the nanoparticle can be preferentially delivered to the CSCs and the second agent can be preferentially delivered to the differentiated cancer cells.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which.

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

The present disclosure is generally directed to systems and methods for targeting different cancer cell types that are present in tumor tissue. More specifically, disclosed systems and methods include a targeting mechanism that preferentially targets CSCs. In one embodiment, a system can include a first component for specifically targeting CSCs and a second component for specifically targeting differentiated cancer cells. According to this embodiment, each component can utilize a different targeting mechanism specific for the subpopulation of cancer cell type.

The systems and methods have been developed through realization that cancer relapse, metastasis, and drug resistance in cancer therapy are related to the resistance to typical cancer therapies of the very small population (generally<1%) of stem cells in the tumor tissue. CSCs and differentiated cancer cells differ in many respects. For instance, CSCs can be identified by markers that are not significantly expressed by differentiated cancer cells. CD44 is a cell membrane glycoprotein involved in cell-cell adhesion and is the most widely used marker to identify CSCs. CD44 is up-regulated in almost all CSCs and blocking CD44 signaling by the addition of CD44 binding peptide reduces maintenance and growth of cancer stem cells. CSCs also express markers of the epithelial to mesenchymal (EMT) transition with up-regulation of the cell-cell adhesion marker N-cadherin and down-regulation of E-cadherin. Other EMT markers that are up-regulated in CSCs include Snail, Slug, Twist, Vim, and ZEB2. Transforming growth factor-β (TGF-β), an inducer of primary tumorigenesis and a positive regulator of tumor progression, is also up-regulated in CSCs. Further, non-cell-adherent matrices support the growth of CSCs whereas cell-adherent matrices or matrices conjugated with cell-adhesive peptides like RGD support the growth of differentiated sub-population of cancer cells.

Another difference between these two sub-populations of cancer cells provides a basis for disclosed CSC-targeted delivery systems and methods. Small molecules such as are commonly used in cancer therapy (e.g., about 1 nm in size or less) are taken up by cancer cells via a passive, activation-controlled, flip-flop mechanism involving drug partitioning to the cell membrane followed by passage through the lipid bilayer. In the case of toxic materials such as cancer drugs, the cell responds by deploying ATP binding cassette (ABC) transporters protein superfamily or efflux pumps to pump the toxic compounds out of the cell cytoplasm and into the extracellular matrix (ECM). These transporters are also called multidrug resistance (MDR) transporters or multidrug resistance protein (MRP) complexes. When the expression of efflux proteins are down-regulated and the efflux pump is not active, the drug concentration in the cell cytoplasm can rise above the toxic level as designed by traditional drug delivery systems and the cells die. However, when the expression of efflux proteins are up-regulated (as is the case for CSCs) and the efflux pump is active, the drug is pumped out and the drug concentration in the cell cytoplasm falls below the therapeutic level and the cells survive. This passive diffusion and efflux by ABC transporter proteins only functions for small molecules such as the cancer drugs Doxorubicin and Paclitaxel.

Figure 1:
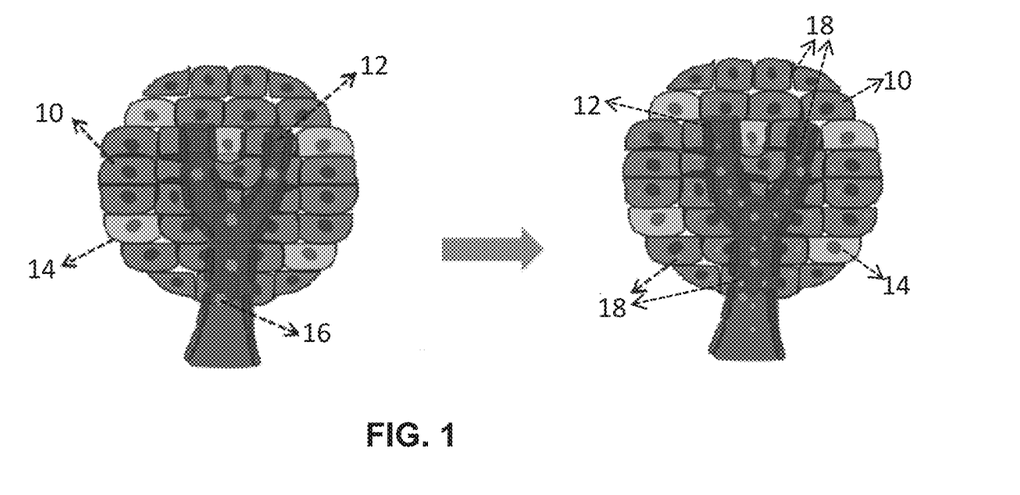
FIG. 1 illustrates a conventional approach for targeting a drug to tumor vasculature.

FIG. 1 schematically illustrates a typical cancer drug targeting system. As shown, a delivery system can use degradable/leaky nanoparticles 16 typically in a size range of from about 100 nm to about 200 nm. The nanoparticles 16 are conjugated/encapsulated with a cancer drug 18 and delivered to the tumor vasculature 12 within a tumor that includes both differentiated cancer cells 10 and cancer stem cells 14 (left). After reaching the vasculature 12 (right), the nanoparticles 16 release the drug 18 which can then diffuse into the interstitial space of the surrounding tumor tissue where the drug is taken up by the bulk (differentiated) cancer cells 10 through passive diffusion to achieve toxic drug levels in the cell cytoplasm. While the drug may also be taken up by the cancer stem cells 14, it is effectively pumped out of the cancer stem cells 14 by the efflux pump mechanism, thus failing to achieve toxic drug levels in the cytoplasm of cancer stem cells.

For differentiated cancer cells 10, the efflux pump in the cell sub-population is not active, the drug concentration remains above the toxic level, and cells die. However, as previously discussed, the ABC transporters of the efflux pump are up-regulated in the undifferentiated sub-population of cancer stem cells 14, thus the drug concentration falls below the toxic level and the cancer stem cells survive traditional therapies. As an example, the expression of ABCG2 efflux protein, also known as BCRP or MXR, in MDA-MB-231 human breast cancer stem cells is up-regulated as well as is the expression of EGFR stem cell marker.

The CSC sub-population is not efficient in retaining free drug and thus can exhibit high survival rates under typical cancer therapies. However, it has been found that nanoparticles in the size range of 5-20 nm can diffuse through the extracellular matrix of the tumor tissue and can be taken up/endocytosed by the cells, specifically cancer stem cells, via macropinocytosis as well as other endocytosis pathways. This realization provides for the approach to cancer therapy according to the disclosed systems and methods. In one embodiment, a multi-dimensional approach to cancer therapy can be provided with a multi-component drug delivery system.

The first component of a drug delivery system can include a typical approach as is illustrated in FIG. 1 that is effective in targeting differentiated cancer cells. This component of a system can include a biologically active agent 18 that is directly or indirectly effective against cancer cells (also termed a drug throughout this disclosure) in a fashion that is effective with differentiated cancer cells. For instance, this component of a two-part system can include a free drug, a drug-antibody conjugate, or a drug encapsulated in degradable/resorbable nanoparticles as illustrated in FIG. 1 for delivery to the differentiated sub-population of cancer cells.

Figure 2:
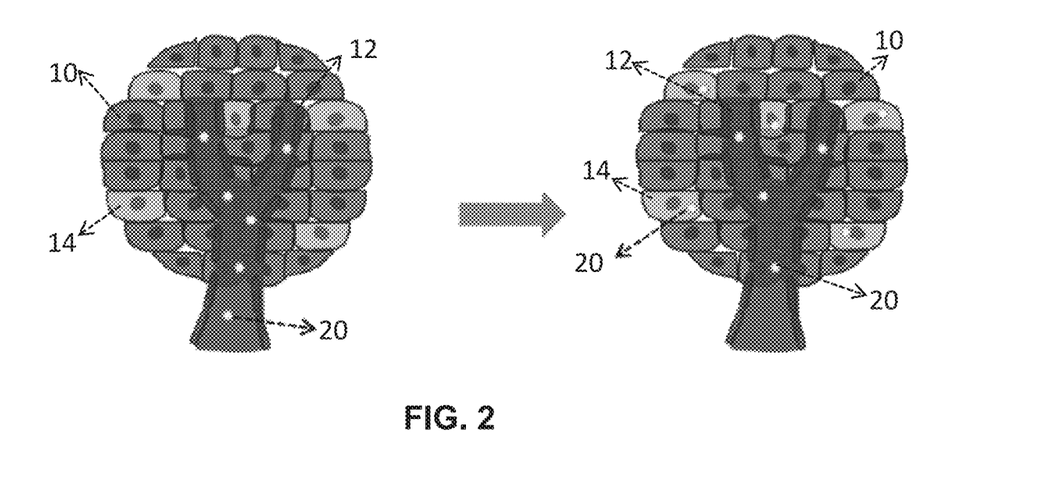
FIG. 2 illustrates a drug targeting system as described herein.

In addition to a typical drug delivery system such as that illustrated in FIG. 1, a multi-component delivery system can also include a component that is configured for targeted delivery of a biologically active agent (e.g., a drug) that is directly or indirectly effective against the cancer stem cells of a tumor tissue and that is schematically illustrated in FIG. 2. This component of a delivery system can include a drug conjugated to a nanoparticle 20 that has been designed for preferential uptake and retention by cancer stem cells. More specifically, a nanoparticle 20 can have a size of from about 5 nm to about 20 nm. The nanoparticles 20 can be delivered to a tumor tissue according to standard practice, for instance via the vasculature 12 as shown in FIG. 2. Following, the nanoparticles 20 can diffuse into the interstitial space of the tumor tissue and the nanoparticles 20 can be selectively taken up by the CSCs 14 via endocytosis, and in particular by macropinocytosis, a mechanism that has not been explored in conventional therapies. Following uptake via macropinocytosis, the drug payload can be released from the nanoparticles 20 by hydrolytic and/or enzymatic action without triggering the efflux pump, leading to the desired toxic effects of the drug on the cancer stem cells.

As is known, cells take up nutrients, proteins, and solid particles by endocytosis, a mechanism different from molecular diffusion. Endocytosis involves bulk transport of the molecules or particles from the extracellular matrix to the cell cytoplasm without diffusion through the lipid bilayer. Endocytosis includes pinocytosis, macropinocytosis, caveolae-dependent endocytosis, clathrin-dependent endocytosis, and phagocytosis. The various methods differ in certain fashions. For instance, pinocytosis is the engulfment of liquids in the extracellular matrix and cell uptake triggered by the intercalation of individual molecules like proteins and antibodies and even drug molecules with the cell membrane. It is used for bulk nutrient and protein uptake by the cell in parallel with diffusion through the lipid bilayer. In contrast to all other endocytotic bulk transports, macropinocytosis is the wrapping of cell membrane around liquids in the ECM and cell uptake triggered by small-scale interaction of particles (multiple interactions at the nanoscale) in the liquid with cell membrane receptors. This mechanism is advantageously utilized for uptake of nanoparticles in the 5-20 nm range by engulfment within 200-500 nm macropinosomes for the selective uptake of cancer drugs by the stem cell sub-population of cancer cells by conjugation of a drug to nanoparticles in the defined size range.

Figure 3:
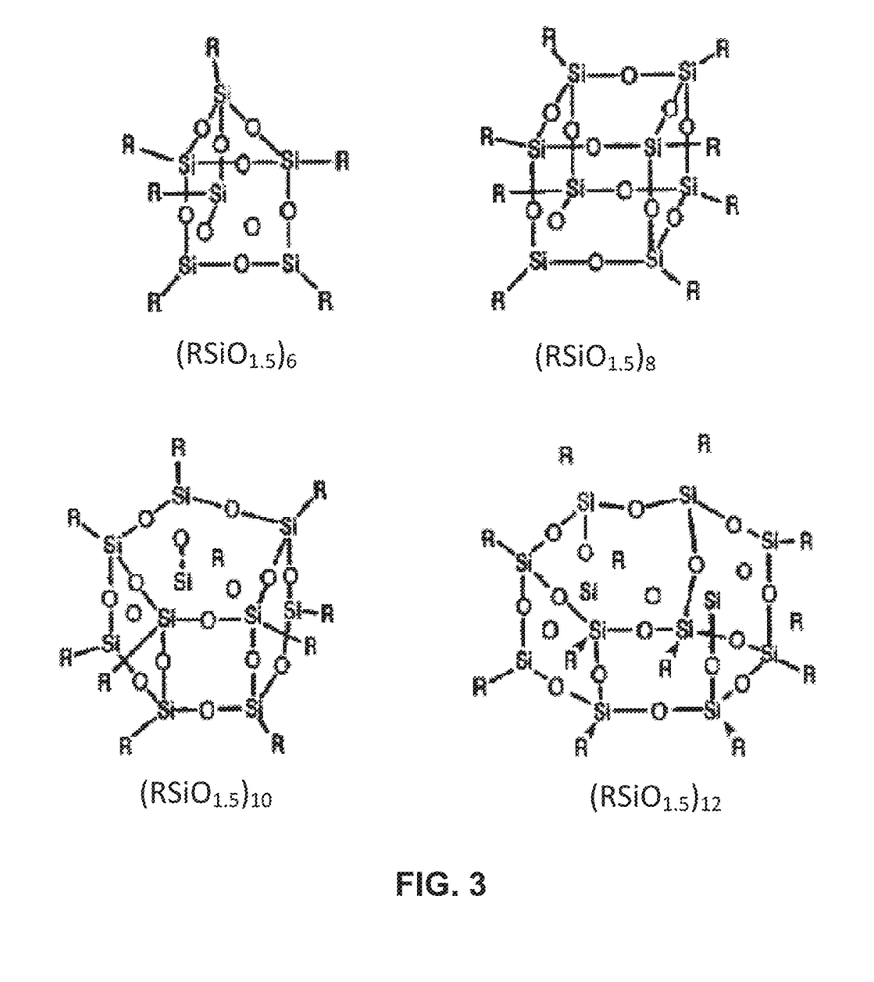
FIG. 3 presents structures of exemplary POSS as may be utilized in forming a conjugated nanoparticle as described herein.

In one embodiment, the nanoparticles can be silica-based nanoparticles, and in one particular embodiment can be based upon a polyhedral oligomeric silsequioxane (POSS). POSS are examples of silsesquioxanes that are functional nanoscale oligomers described by the specific formula $(RSiO_{1.5})_n$, wherein R indicates an organic group including but not limited to hydrogen, alkyl, aryl, halogen, or alkenyl groups, as well as combinations and derivatives thereof. Typically, the POSS structure includes an eight corner cage bearing one or more functional groups. Typical structures of POSS encompassed herein in which n has a value of 6, 8, 10, or 12, are illustrated in FIG. 3, though other n values are contemplated herein.

POSS nanoparticles can be prepared according to known methodology, for instance by hydrolysis and subsequent condensation of trifunctional silanes in slightly elevated or room temperature using a basic or acidic catalyst. Precursors can include silanes having the general structure of $RSiX_3$ (X=Cl, OR, OAc, $NH_2$, etc.) that are relatively easy to hydrolyze providing silanol groups and can be further subjected to polycondensation. Hydrolysis rate can depend on the type of substituent that is present on the silica atom (i.e., bigger substituent=lower rate) and type of functional group X. Temperature, monomer concentration, amount of water added, type of solvent and catalyst can also influence the formation efficiency. Polycondensation can be performed in such a manner to provide any of a variety of structures, examples of which are presented in FIG. 3. POSS nanoparticles can be particularly useful as they can be formed to a well-defined size and include a highly stable inorganic silicate core that confers rigidity and stability and an organic exterior that can be easily conjugated with an agent for delivery to CSCs.

POSS nanoparticles can be formed to be quite small and therefore can be diffusible in the interstitial space of the tumor tissue and able to reach the cancer stem cells where they are endocytosed by the stem cells prior to the release of the drug. This approach can provide for more effective intracellular delivery of a drug to the CSCs as opposed to extracellular delivery of conventional therapies that can be effective against differentiated cancer cells.

The nanoparticles for targeting to the CSCs can be conjugated with a drug via suitable reactive functionality of the nanoparticle material. For instance, a POSS nanoparticle can be formed from a functionalized silane, the functionality of which (i.e., an R-group) can react with a reactive functionality of an agent to be delivered to the CSCs and thereby the agent can be conjugated to the nanoparticle. In general, the conjugation reaction can be one in which the drug can either retain desired functionality upon conjugation or can be released from the nanoparticle following CSC take-up, for instance via hydrolysis or enzymatic action. By way of example, a POSS nanoparticle including an amine functionality can be combined with a drug to be delivered that includes (or is functionalized to include) a carboxylic acid functionality so as to conjugate the drug to the carrier by the formation of an amide bond. A non-limiting list of conjugation reactions which can be used can include amine-succinimide conjugation reaction, amine-carboxylic acid conjugation reaction, Michael's addition reaction (e.g., acrylate-cysteine), thiol-maleimide conjugation reaction, click conjugation reaction (e.g., propargyl-azide), and the oxime conjugation reaction (aldehyde-amine).

In one embodiment, the CSC targeted delivery component can be combined with a more conventional therapy that shows good efficacy against differentiated cancer cells. For instance, a multi-component delivery system can combine the CSC-targeted nanoparticles with a free drug for delivery to the vasculature of tumor tissue.

In one embodiment, a second component of a system that is configured to target differentiated cancer cells can include a delivery/targeting component that can improve targeting of the drug to the cancer cells of a tumor tissue. For instance, a second component of a system can incorporate larger degradable or leaky nanoparticles as are known that can encapsulate and target drugs to the tumor vasculature.

In one embodiment, a cancer drug can be encapsulated in liposomes or other lipid-based complexes for delivery to tumor vasculature. Liposomes can be useful as drug carriers due to their flexible nature in terms of composition, size and preparation method. Liposomes have an aqueous inner volume and a hydrophobic volume within the bilayer, and as such can be utilized in the delivery of both hydrophobic and hydrophilic agents. In general, liposomes are self-assembling phospholipid bilayer structures that can be prepared from natural or synthetic phospholipid sources. Liposomes can encapsulate water soluble molecules in the aqueous volume and water insoluble molecules can be embedded in the hydrophobic region of the lipid bilayer.

Liposomes can be prepared according to known methods, for instance via the thin lipid film hydration method as is generally known in the art. The constituents of a liposomal delivery system are the primary determinants of the preparation method to be employed. For instance, when incorporating hydrophobic molecules, they can be included during the lipid film formation process (passive loading), whereas water soluble molecules can be introduced during the hydration step (passive loading) or incorporated later on by active loading procedures using ion gradients.

The phospholipid backbone of liposomes can include saturated or unsaturated phospholipids and generally include acyl chain length of from about 14 to about 20 carbons. Surface modification with hydrophilic polymers is encompassed in liposomal delivery systems. For instance, polyethylene glycol (PEG) molecules of various chain lengths can be used to provide a protective shield over the phospholipid bilayer. PEG may be useful as, among other benefits, it possesses hydroxyl groups available for further derivatization if desired.

In one embodiment, degradable nanoparticles for delivery of an active agent to tumor tissue can be formed from polymeric matrices; examples of which can include, without limitation, polyethylenes, polycarbonates, polyanhydrides, polyhydroxyacids, polypropylfumerates, polycaprolactones, polyam ides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, or polyamines, or combinations thereof. For instance, nanoparticles can include a matrix based upon a polyalkylene glycol such as polyethylene glycol. In one embodiment, a polyester-based nanoparticle can be utilized, for instance a polyester selected from poly(lactide-co-glycolide) (PLGA), poly (lactide) (PLA), poly(glycolide) (PGA), and polycaprolactones (PCL). A polymeric matrix can optionally include a copolymer of two or more polymers, for example a copolymer of a polyalkylene glycol and a polyester such as a copolymer of PEG and PLGA or PLA. A degradable nanoparticle can encapsulate an active agent through covalent or non-covalent bonding (e.g., ionic bonding) or merely through physical encapsulation within the matrix.

A drug-antibody conjugate can be utilized to preferentially target a drug to cancer cells rather than healthy cells via specificity of an antibody for particular cancer cell surface receptors. Moreover, a drug-antibody conjugate can be delivered in conjunction with a nanoparticle delivery agent or independent of a larger delivery agent. Further, a drug delivery system can use one or multiple different drugs and can target multiple cell surface receptors or multiple intercellular pathways to trigger cell death as is known.

Moreover, it should be understood that the disclosed CSC-targeting delivery system can be utilized in conjunction with any other cancer treatment therapy as is known and is not limited to the particular examples described herein.

Any cancer drug and any type of cancer cell subpopulation are encompassed herein. As utilized herein, the term "cancer drug" generally refers to any agent useful to combat cancer, either directly or indirectly. Moreover, a delivery system can include one or more different cancer drugs. For instance, a CSC-targeting component of a system can include a first agent specifically configured for effectiveness against CSCs and a second component of a system can include a different agent that is specifically configured for effectiveness against one or more different cell subpopulations of the tumor tissue. Moreover, multiple agents can be provided by a system for targeting one or more of the different cell subpopulations of tumor tissue. A non-limiting list of cancer drugs that can be delivered by use of disclosed systems can include those described by, for example, U.S. Pat. No. 5,037,883, which is incorporated herein by reference. U.S. Pat. Nos. 6,348,209, 6,346,349, and 6,342,221 also describe agents related to cancer drugs, all of which are incorporated herein by reference.

Classes of active agents encompassed herein include, but are not limited to, chemotherapeutic agents, cytotoxins, antimetabolites, alkylating agents, protein kinase inhibitors, anthracyclines, antibiotics, antimitotic agents (e.g. antitubulin agents), corticosteroids, radiopharmaceuticals, antibodies, and proteins (e.g. cytokines, enzymes, or interferons). Active agents can include, for example, small molecule organic compounds, macromolecules, metal containing compounds, and compounds or chelates that include radionuclides. Specific examples of small molecule organic compounds include, but are not limited to docetaxel, gemcitabine, imatinib (Gleevec®), 5-fluorouracil, 9-aminocamptothecin, amine-modified geldanamycin, doxorubicin, paclitaxel (Taxol®), cisplatin, procarbazine, hydroxyurea, meso e-chlorin, Gd(+3) compounds, asparaginase, and radionuclides (e.g $I^{131}$, $Y^{90}$, $In^{111}$, and $Tc^{99m}$). There are many cancer drugs known in the art and many continue to be developed.

By way of example, in one embodiment, Paclitaxel (PTX) can be encapsulated in liposomes to target differentiated cancer cells and this component can be delivered to tumor tissue in combination with PTX conjugated to POSS nanoparticles to target cancer stem cells. The PTX-liposome component is selectively taken up by tumor vasculature followed by the release of PTX to the tumor tissue and uptake by differentiated cancer cells. The POSS nanoparticles that include conjugated PTX is likewise be taken up by tumor vasculature, but thereafter diffuses into the interstitial space of the tumor followed by macropinocytosis of the POSS nanoparticles by the CSCs. Following macropinocytosis, the PTX can be released from the POSS nanoparticles and retained in the CSCs in a toxic concentration.

The CSC-targeting delivery system can be used with any cancer type including breast, lung, colon, gastric, liver, thyroid, bladder, oral, ovarian, nasal to name a few and in one particular embodiment, in treatment of cancers with a high fraction of cancer stem cells.

The present disclosure may be better understood with reference to the Examples set forth below.

EXAMPLE 1

Figure 4A:
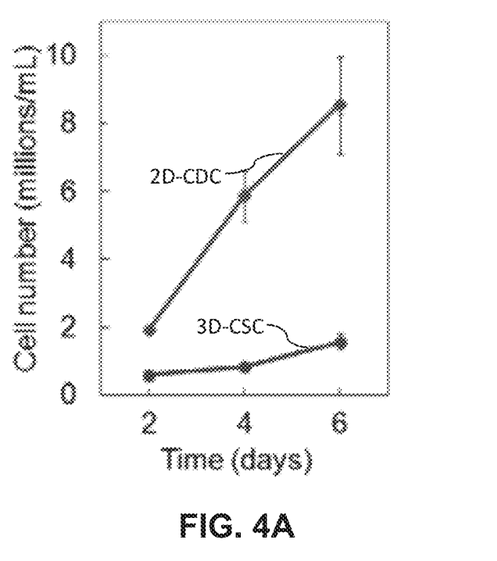
FIG. 4A presents a comparison of the number density with time of MDA-MB-231 (MDA) human breast cancer cells in a 2D adherent culture plate and in a 3D non-adherent matrix.
Figure 4B:
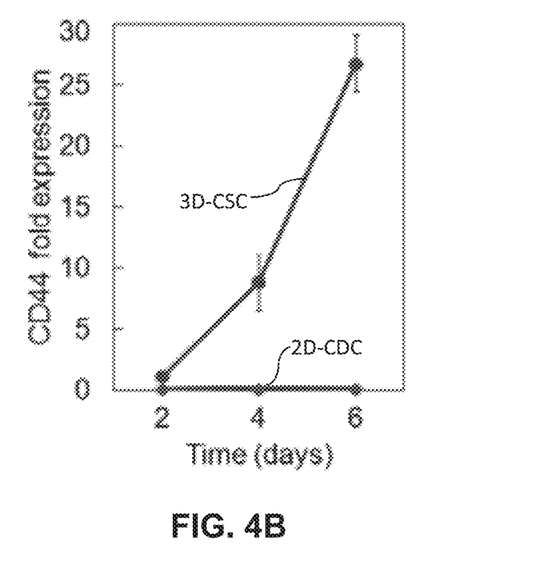
FIG. 4B presents a comparison of the expression of CD44 marker as a function of incubation time for MDA cells in a 2D adherent culture plate and in a 3D non-adherent matrix.
Figure 4C:
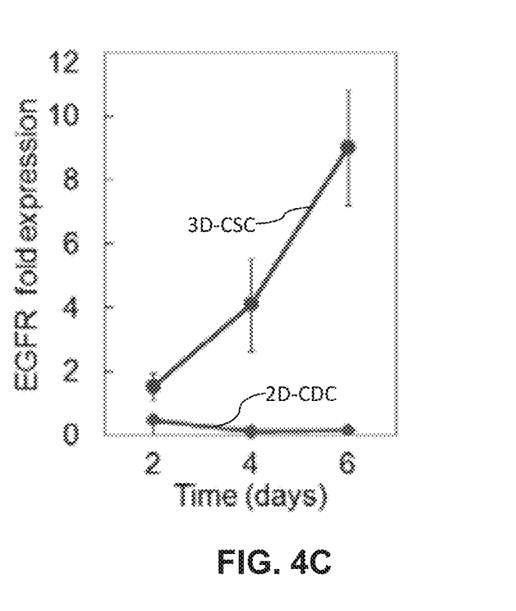
FIG. 4C presents a comparison of the expression of EGFR marker as a function of incubation time for MDA cells in a 2D adherent culture plate and in a 3D non-adherent matrix.
Figure 4D:
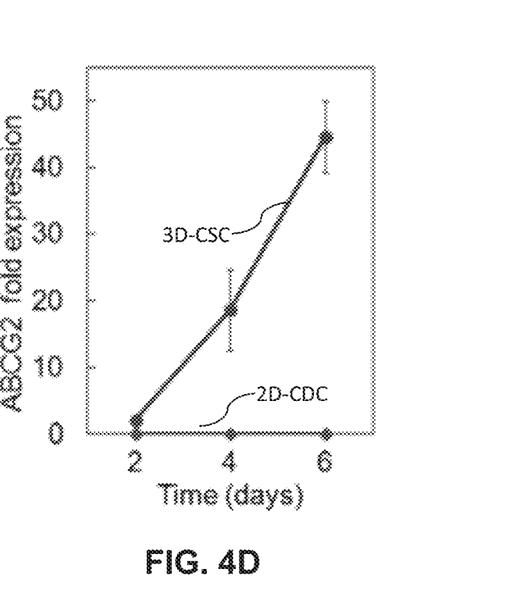
FIG. 4D presents a comparison of the expression of ABCG2 marker as a function of incubation time for MDA cells in a 2D adherent culture plate and in a 3D non-adherent matrix. Error bars in FIG. 4A-FIG. 4D correspond to means±1 SD for n=3.

MDA-MB-231 human breast cancer cells were cultured on 2D adherent polystyrene culture plates that enriched the differentiated cell sub-population (CDC) and in 3D polyethylene glycol diacrylate crosslinked non-adherent matrix that enriches the stem sub-population (CSC). FIG. 4A-4D compare cell content and the expression of CD44, ABCG2, and EGFR markers as a function of time. As can be seen, the differentiated cancer cells grew, relatively rapidly, on adherent 2D culture plates whereas the cancer stem cells grew, relatively slowly, in the 3D non-adherent gels as stem-like cells have a longer cell cycle time or doubling time (FIG. 4A). The MDA-MB-231 cells grown on 2D culture plates showed almost no expression of CSC marker CD44 whereas the cells grown in the 3D matrix showed intense expression of CD44 (FIG. 4B) with culture time. Further, the cells grown on the 2D plates showed very low expression of stem cell marker EGFR whereas the cells grown in the 3D matrix showed sharp increase in EGFR expression with culture time (FIG. 4C). Furthermore, the cells grown on 2D plates showed no expression of ABC efflux protein marker ABCG2 whereas those grown in 3D gel showed a sharp increase in ABCG2 expression (FIG. 4D).

These results clearly demonstrate that there were two distinct cell subpopulations in the cancer cells with one population having relatively low expression of ABC transporters and the other with relatively high expression of ABC transporters.

Figure 5A:
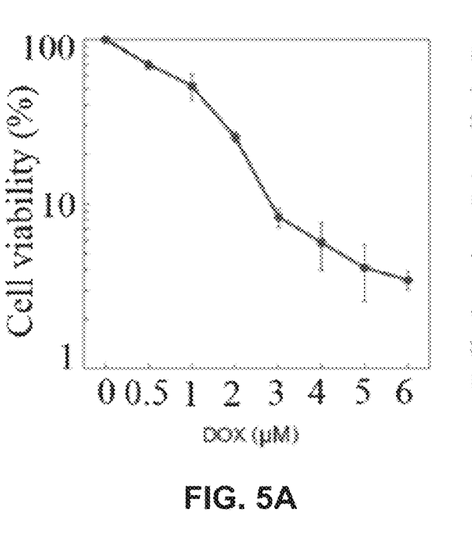
FIG. 5A presents the cell viability (in percent) of MDA cells cultured on a 2D culture plate as a function of increasing doxorubicin (DOX) concentration.

FIG. 5A-FIG. 5D show the response of the MDA-MB-231 human breast cancer cells cultured in 2D adherent plates and 3D non-adherent matrix to treatment with Doxorubicin (DOX) cancer drug. For the 2D culture, cell viability decreased exponentially as the drug concentration increased (FIG. 5A) and reached about 5% as the drug concentration was increased to 5 µM. FIG. 5A indicates that DOX is effective in removing 95% of the cells with the understanding that the differentiated cells with low expression of ABC transporter proteins dominate the 2D culture.

Figure 5B:
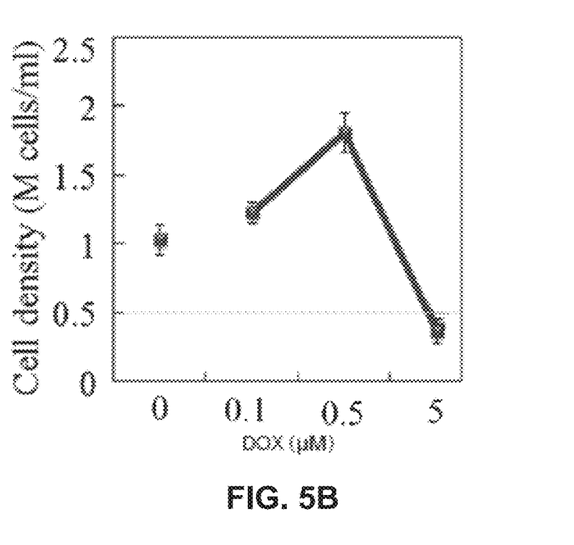
FIG. 5B presents the cell viability (in cells/m L) of MDA cells cultured in 3D matrix as a function of increasing DOX concentration.
Figure 5C:
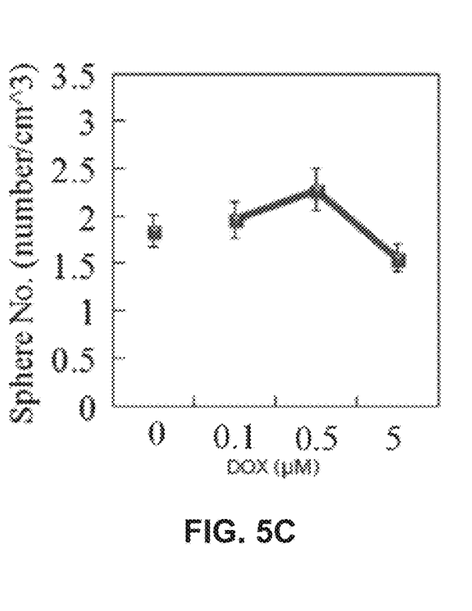
FIG. 5C presents the number of MDA tumor spheres remaining in a 3D matrix as a function of DOX concentration.

For the 3D matrix, cell viability first increased with drug concentration of 0.5 µM before decreasing to 35% at 5 µM DOX concentration (FIG. 5B), the number of tumorspheres in the 3D matrix first increased with 0.5 µM DOX concentration before decreasing to only 85% of the initial number of tumorspheres (FIG. 5C). In addition, the expression of CSC marker CD44 dramatically increased at higher DOX concentrations (FIG. 5D).

Figure 5D:
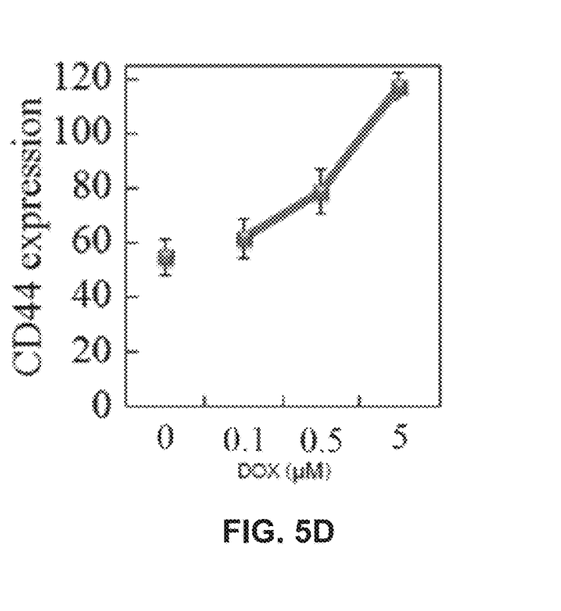
FIG. 5D presents the expression of CSC marker CD44 for MDA cells cultured in the 3D matrix as a function of DOX concentration.

FIG. 5B-FIG. 5D indicate that DOX was not effective when MDA-MB-231 cancer cells were cultured in 3D non-adherent matrix in which the stem cell sub-population with high expression of ABC transporter proteins dominate the culture. These results further demonstrate that the efflux pumps effectively reduce the concentration of DOX in the cell to below the toxic level and that passive diffusion is not an effective mechanism for DOX delivery to the stem cell sub-population of MDA-MB-231 cancer cells.

EXAMPLE 2

The following approach was used to synthesize octa (3-aminopropyl) octasilsequioxane octahydrochloride nanoparticles, hereafter referred to as POSS-NH$^{3+}$ NPs: A solution of 350 mL methanol and 30 mL concentrated HCl (35% HCl) was charged to a 1000 mL two-neck reaction flask equipped with a reflux condenser and a magnetic stirrer. Next, 15 mL (60 mmol) (3-aminopropyl)-triethoxysilane was added dropwise to the reaction flask at 60° C. with mixing. Following, the reaction mixture was heated to 90° C. in an oil bath and the reaction was refluxed for 16 h with vigorous stirring.

After completion, the reaction was cooled to ambient condition and 300 mL of tetrahydrofuran (THF) was added to the reaction mixture to precipitate the product. The product was collected by filtration, washed 3 times with THF and POSS-NH$^{3+}$ product was collected as a white powder. The reaction yield was 33%. The characterization data for POSS-NH$^{3+}$ is as follows: FT-IR (KBr, cm$^{-1}$): 3224, 3025, 1604, 1494, 1122, 935 cm$^{-1}$; $^1$H-NMR (400 MHz, D$_2$O): δ 2.91(t, CH$_2$NH$_3$, 16H), 1.68 (m, SiCH$_2$CH$_2$, 16H), 0.68 (t, SiCH$_2$, 16H).

The following approach was used to synthesize Taxol-2'-hemisuccinate, hereafter referred as PTX-COON: 0.3 g of succinic anhydride was added to 5 mL of PTX solution in dry pyridine (0.4 g/mL PTX) to reach succinic anhydride/PTX molar ratio of 12.5:1. The reaction was allowed to continue at ambient condition for 3 h and the progress of the reaction was monitored by thin-layer chromatography (TLC, CH$_3$COCH$_3$:CHCl$_3$ v/v of 1:1). Next, the solvent was evaporated under vacuum and the residue was suspended in 16 mL of distilled water, stirred for 30 min, and centrifuged. The residue after centrifugation was dissolved in acetone and precipitated in water. The absence of unreacted PTX was verified by TLC. The white crystals collected after filtration had a purity of 95%. Mass spectrometry of the powder showed a peak at 954 mass number.

The following approach was used to synthesize PTX conjugated to POSS (PTXconjPOSS) nanoparticles: 50 mg PTX-COON (50 µmol), 30 µL triethylamine and 20 mg 4-(4,6-Dimethoxy-1,3,5-triazin-2-yl)-4-methylmorpholinium chloride (DMTMM, 60 µmol) were stirred in 2 mL dry DMSO until complete dissolution of the solids. Next, 20 mg POSS-NH$^{3+}$ (17 µmol) was added to the reaction mixture and the reaction was allowed to proceed at ambient condition under stirring for 24 h under argon atmosphere. After completion of the reaction, the resulting mixture was poured into 45 mL acetonitrile containing 0.1% HCl with vortexing to precipitate the product. The product PTXconjPOSS was collected by vacuum filtration and characterized.

Figure 6A:
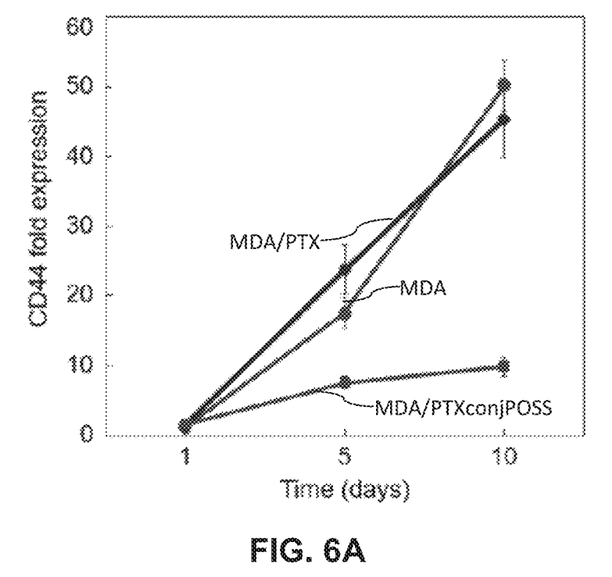
FIG. 6A presents the expression of CSC marker CD44 for MDA cells cultured in a 3D matrix in response to treatment with Paclitaxel (PTX) or PTX conjugated to POSS nanoparticles (PTXconjPOSS).
Figure 6B:
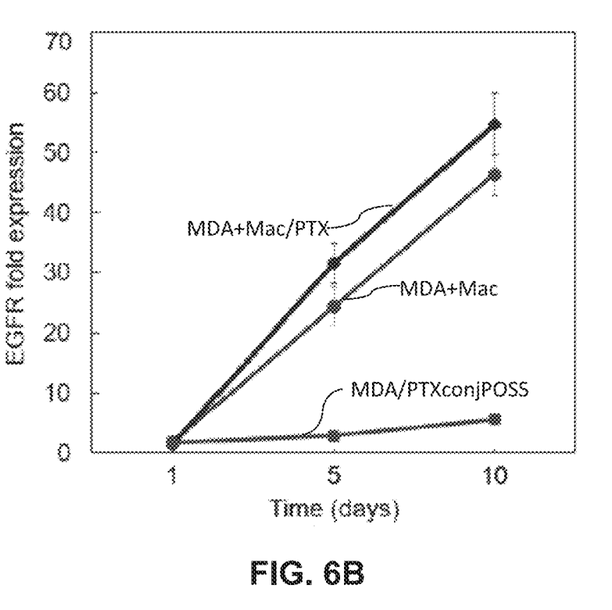
FIG. 6B presents the expression of stem cell marker EGFR for MDA cells cultured in a 3D matrix in response to treatment with PTX or PTX conjugated to POSS nanoparticles (PTXconjPOSS).

FIG. 6A and FIG. 6B show the expression of CSC markers CD44 and EGFR, respectively, of MDA-MB-231 (MDA) human breast cancer cells grown in a 3D non-adherent matrix as described in Example 1 above after exposure to free Paclitaxel (PTX) or PTX conjugated to POSS nanoparticles (PTXconjPOSS) as a function of incubation time. MDA cells cultured in the 3D matrix without exposure to PTX showed very high expression of CD44 and EGFR. MDA cells exposed to free PTX also showed very high expression of CD44 and EGFR at a level similar to MDA cells without PTX exposure. Conversely, MDA cells cultured in the 3D non-adherent matrix and exposed to PTXconjPOSS showed much lower expression of CD44 and EGFR compared to the cells exposed to free PTX. The results demonstrate that PTX conjugated to POSS nanoparticles was toxic to CSCs whereas free PTX was not toxic to CSCs. On the other hand, free PTX was effective against the differentiated sub-population of cancer cells but not the CSC sub-population. These results demonstrate that a multiprong therapy that includes a combination of free PTX and PTXconjPOSS can effectively eliminate both the differentiated and the CSC populations of cancer cells.

While certain embodiments of the disclosed subject matter have been described using specific terms, such description is for illustrative purposes only, and it is to be understood that changes and variations may be made without departing from the spirit or scope of the subject matter.

What is claimed is:

1. A drug delivery system comprising: a first component for targeting cancer stem cells, the first component comprising a first biologically active agent that directly or indirectly affects the cancer stem cells conjugated to a first nanoparticle, the first nanoparticle having a size of from 5 nanometers to 20 nanometers; and a second component for targeting differentiated cancer cells, the second component comprising a second biologically active agent that directly or indirectly affects the differentiated cancer cells, wherein the second biologically active agent is encapsulated in or conjugated to a second nanoparticle having a size of from about 100 nm to about 200 nm, is in the form of a free drug.

2. The drug delivery system of claim 1, wherein the first nanoparticle comprises a polyhedral oligomeric silsequioxane.

3. The drug delivery system of claim 2, the polyhedral oligomeric silsequioxane comprising a structure of $RSiO_{1.5}$, in which R is a hydrogen, an alkyl group, an aryl group, a halogen, an alkenyl group, or a combination thereof.

4. The drug delivery system of claim 3, the polyhedral oligomeric silsequioxane comprising a structure of $(RSiO_{1.5})_n$, in which n has a value of 6, 8, 10, or 12.

5. The drug delivery system of claim 1, wherein the second biologically active agent is the same as the first biologically active agent.

6. The drug delivery system of claim 1, wherein the second biologically active agent is different than the first biologically active agent.

* * * * *